May 17, 1955
O. A. KAUSEN
Plant Pat. 1,394
AZALEA PLANT
Filed June 11, 1953
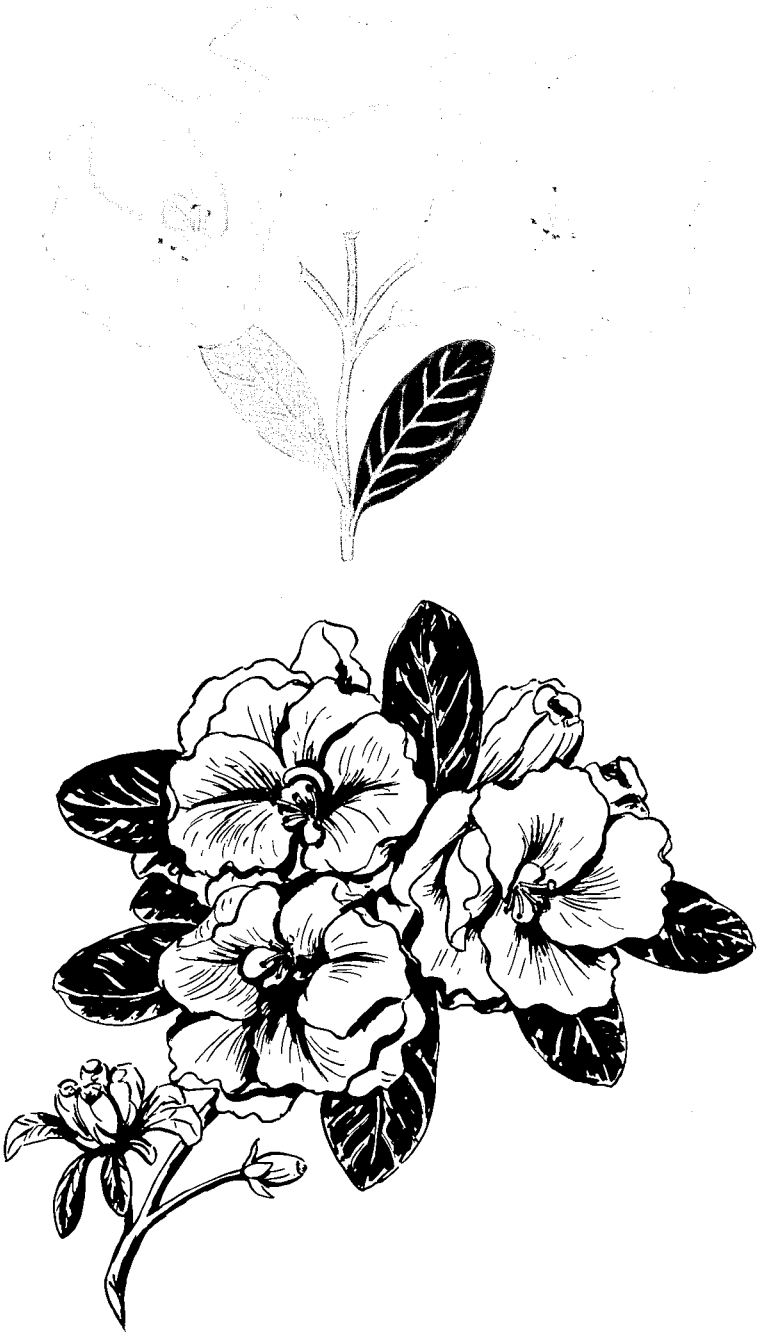
INVENTOR.
Otto A. Kausen
BY
Attorney United States Patent Office Plant Pat. 1,394

Patented May 17, 1955

1,394

AZALEA PLANT

Otto A. Kausen, Eureka, Calif.

Application June 11, 1953, Serial No. 361,104

1 Claim. (Cl. 47—60)

This invention and discovery relates to a new and distinct variety of azalea plant and more particularly relates to a new and distinct variety of azalea plant of the species *Azalea indica.*

Broadly, this new variety of azalea plant is distinguishable from the parent plant, as well as from other known varieties mainly by the form and color of the hose in hose type of corolla, the petals of which are ruffled and convexly scalloped at the peripheral edge.

This new variety has a profuseness of bloom which, at the optimum of season and plant growth, form a rosette blanket or canopy effect above the foliage which lies thereunder. It is also characteristic of this new variety that the bloom has exceptional lasting quality and that the young plants set flower buds very early and very freely, adding substantially to the advantages of this new variety for marketing early in its period of growth.

The accompanying illustration forming a part of this specification shows in one view in black and white a substantial portion of the new variety and in another view in color several of the blooms with foliage leaves.

The colors mentioned herein correspond approximately to those shown in "Horticultural Color Chart" issued by the British Color Council in collaboration with the Royal Horticultural Society, such colors being more specifically identified by the color name and plate of said color standard by recapitulation in tabular form herein.

This new variety is a sport mutation of an azalea plant of a variety known in the trade as azalea "Simon Mardner," unpatented, and which has been well known by that name for more than 20 years by those conversant with the horticultural art.

This new variety was originated and discoered by me in a glass house under my supervision and control at Eureka, Humboldt County, California, and has been carefully watched, cultivated and nurtured by me. This new variety has been asexually reproduced by me at Eureka, California, from cuttings, through four generations, and has remained true to its original type and the herein described characteristics through the propagation of several thousand plants over a period of four years, and has shown its qualities and characteristics to be permanently fixed.

In physical structure the main trunk is strong and rugged and the exterior is roughly wooded with bark, the vegetative growth of branches from the main trunk being irregular in direction as characteristic of the azalea plant Simon Mardner. The inflorescence forms at the tips of the new wood of the branches and the flowers are supported by short, fleshy-like green pedicels upon the end of which forms a sub-pubescent ovary of medium green color. The flower has a funnel-shaped dual corolla of China Rose color which is seated upon the pedicels, the style and stamens extending into the corolla as usual. Each flower has two corolla, one telescoped within the other, and known as the hose in hose type; each corolla has five petals convexly scalloped and ruffled at the edge portion, the petals being gamopetalous at their base with relation to the corolla from which they grow as an integral part.

More specifically, the following is a detailed description of this new variety:

PARENTAGE

Origin: Sport mutation.

Parentage: Parent variety: *Azalea indica,* known as Simon Mardner.

INFLORESCENCE

Blooming habit: Annually from early winter to spring months, December to April, depending on climatic and temperature conditions, a temperature approximately 65° being preferable for blomming. The young plants set buds very early in growth, usually as early as the second year, and are therefore marketable early in growth.

FLOWERS

Buds:

*Size.*—About ¼ inch and gradually growing in length with unfolding of overlapping petals.

*Petals.*—Color, a pale China Rose in the bud.

*Set of buds.*—Sets buds freely and profusely in young plants in second year of growth.

Bloom:

*Size.*—Large and full, average 2 inches between opposite tips of petals.

*Borne.*—Clusters of 3 to 6 on short fleshy pedicels growing from end tip of new wood peduncles; corymbose, compact, profuse at optimum of growth and bloom, forming a rosette blanket of blooms over the underlying foliage and vegetative growth.

*Form.*—Two corolla to each bloom, the corolla being of funnel form varying 1½ inch to 2 inches in length, one telescoped within the other and known in the floricultural art as hose in hose type, the petals growing integrally from the corolla.

*Color.*—Petals and corolla are of China Rose color, and exceptionally uniform in color.

*Petalage.*—Gamopetalous; 5 petals to each of the two telescoped corolla; petals convexedly scalloped and excessively ruffled at the peripheral edge.

*Fragrance.*—Substantially none.

*Persistence of bloom.*—Deciduous; lasting quality exceptionally good, two to three weeks, assuming reasonable care and moisture.

*Texture of bloom.*—Petals and corolla are satin luster on obverse face and more subdued on reverse face.

*Other features of bloom.*—Usually 1 to 4 small petals at the center of dual corolla which are independent of the corolla and of each other, and of color similar to the corolla.

Genital organs:

*Stamens.*—5 in number; color of filament pale pink; color of anthers dark violet purple.

*Pistil.*—Style substantially same length as stamens; color pale green; stigma light lettuce green.

*Ovary.*—Apparently single and single ovule; exterior slightly pubescent; color lettuce green.

PLANT (Other than Inflorescence)

Form of plant:

*Size.*—At optimum, 12 to 18 inches high from ground; 12 to 18 inches diameter at crown of massed inflorescence.

Vegetative growth:

*Main trunk.*—Sturdy, strong, rough woody bark.

*Branches.*—Irregular in direction.

*Peduncles.*—Generally straight; growing from tip of the old wood; lettuce green color, at the end of which the flower cluster blooms.

Foliage leaves:

*Shape.*—Prolately ovate elliptical; peripheral edge smooth; texture, subcoriaceous.

*Color.*—Obverse, dark green; reverse medium green.

*Petioles.*—Short, fleshy and tough; color pale green.

*Venation of foliage leaves.*—Petiole extends into midrib and the venation is reticulate.

Asexual reproduction: By cuttings of vegetative growth taken in spring or early summer (in mild cool humid climates, such as Pacific Coast territory); may also be grafted, preferably setting the graft in January; desired soil characteristic, acid, preferably pH 4.5 to 5.5.

The color designations according to the color plates of said "Horticultural Color Chart" are recapitulated in tabular form as follows:

| Element | Color | Sheet | Plate Number |
|---|---|---|---|
| Inflorescence: | | | |
| Buds— | | | |
| Petals | China Rose | 111 | o24/2 |
| Bloom: | | | |
| Corolla and petals | do | 111 | o24/1 |
| Genital Organs: | | | |
| Stamens— | | | |
| filament | Rose Pink | 126 | 427/3 |
| anthers | Violet Purple | 161 | 733 |
| Pistil— | | | |
| style | Lavender Green | 196 | ooo761/3 |
| stigma | Lettuce Green | 176 | 861/3 |
| Ovary | do | 176 | 861 |
| Vegetative Growth: | | | |
| Peduncles | do | 176 | 861/2 |
| Foliage Leaves: | | | |
| Obverse | Ivy Green | 200 | oooo1060 |
| Reverse | Fern Green | 186 | o862/1 |
| Petioles | do | 186 | o862/3 |

Having described and illustrated this new variety of azalea plant, what is claimed as new and patentable is:

A new and distinct variety of azalea plant substantially as illustrated and described, characterized by an inflorescence of flowers having hose in hose dual corolla one corolla telescoped within the other, the petals of the bloom growing from each corolla as an integral part thereof, the petals having convexedly scalloped and ruffled peripheral edges, the corolla and petals being of China Rose color; and further characterized by a setting of buds at an exceptionally early age of growth of the plant.

No references cited.